(12) United States Patent
Staib et al.

(10) Patent No.: US 10,194,839 B2
(45) Date of Patent: Feb. 5, 2019

(54) METHOD AND DEVICE FOR ASSESSMENT OF A SERIES OF GLUCOSE CONCENTRATION VALUES OF A BODY FLUID OF A DIABETIC FOR ADJUSTMENT OF INSULIN DOSING

(75) Inventors: Arnulf Staib, Heppenheim (DE); Hans-Martin Klötzer, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 2251 days.

(21) Appl. No.: 11/422,126

(22) Filed: Jun. 5, 2006

(65) Prior Publication Data
US 2007/0016127 A1    Jan. 18, 2007

(30) Foreign Application Priority Data

Jun. 4, 2005  (EP) .................................. 05 012 091
Jul. 16, 2005  (DE) ........................ 10 2005 033 357

(51) Int. Cl.
| | |
|---|---|
| G01N 33/50 | (2006.01) |
| A61B 5/145 | (2006.01) |
| G01N 33/66 | (2006.01) |
| A61M 5/172 | (2006.01) |
| A61M 5/142 | (2006.01) |

(52) U.S. Cl.
CPC ......... *A61B 5/14532* (2013.01); *G01N 33/66* (2013.01); *A61M 5/1723* (2013.01); *A61M 2005/14208* (2013.01); *G01N 2800/042* (2013.01)

(58) Field of Classification Search
None
See application file for complete search history.

(56) References Cited

U.S. PATENT DOCUMENTS

| | | | |
|---|---|---|---|
| 4,731,726 A | | 3/1988 | Allen, III |
| 5,822,715 A | * | 10/1998 | Worthington et al. ......... 702/19 |
| 2004/0204868 A1 | * | 10/2004 | Maynard et al. ............... 702/30 |
| 2004/0225205 A1 | * | 11/2004 | Fine et al. .................... 600/316 |
| 2005/0177398 A1 | * | 8/2005 | Watanabe et al. ................ 705/3 |
| 2005/0240356 A1 | * | 10/2005 | Staib et al. .................... 702/19 |

FOREIGN PATENT DOCUMENTS

| | | |
|---|---|---|
| EP | 1 281 351 A2 | 2/2003 |
| EP | 1 281 351 A3 | 2/2003 |
| JP | 2001212114 A | 8/2001 |
| JP | 2004000555 A | 1/2004 |
| WO | 2004/023972 A2 | 3/2004 |
| WO | WO 2004/043230 A2 | 5/2004 |

OTHER PUBLICATIONS

Naomi Weintrob, MD et al., "Glycemic Patterns Detected by Continuous Subcutaneous Glucose Sensing in Children and Adolescents with Type 1 Diabetes Mellitus Treated by Multiple Daily Injections vs Continuous Subcutaneous Insulin Infusion," *Arch Pediatr Adolesc Med*, vol. 158, pp. 677-684 (Jul. 2004).
National Institute of Standards and Technology, Croarkin, Carroll and Paul Tobias, Eds., *Nist/Sematech e-Handbook of Statistical Methods*, Chapter 4, Section 1.4.4., available at http://www.itl.nist.gov/div898/handbook/, last accessed on Mar. 20, 2012, 4 pages.

* cited by examiner

*Primary Examiner* — Jason M Sims
(74) *Attorney, Agent, or Firm* — Faegre Baker Daniels LLP

(57) ABSTRACT

The invention relates to a method for assessment of a series of glucose concentration values of a body fluid of a diabetic for adjustment of the dosing of insulin administrations as well as a suitable device for carrying out the method.

19 Claims, 3 Drawing Sheets

METHOD AND DEVICE FOR ASSESSMENT OF A SERIES OF GLUCOSE CONCENTRATION VALUES OF A BODY FLUID OF A DIABETIC FOR ADJUSTMENT OF INSULIN DOSING

REFERENCE TO RELATED APPLICATIONS

The present application is based on German Patent Application No. 10 2005 033 357.5, filed Jul. 16, 2005 which claims priority to European Patent Application No. 05 012 091.4, filed Jun. 4, 2005, which are hereby incorporated by reference in their entirety.

TECHNICAL FIELD

The invention relates to a method for assessment of a series of glucose concentration values of a body fluid of a diabetic for adjustment of the dosing of insulin administrations as well as a suitable device for carrying out the method.

BACKGROUND

Serious long-term secondary effects of diabetes mellitus (for example blindness due to retinopathy) can be prevented only by keeping the blood sugar level within narrow limits, corresponding to those of a healthy person, at all times by means of exactly dosed administrations of insulin. For this reason, insulin-dependent diabetics need to measure their blood glucose concentration several times daily and self-administer the required quantity of insulin.

The optimal dosing of insulin administrations, in terms of quantity and frequency, cannot be derived without further ado from measuring values of the blood glucose concentration. In practical application, the selected dosing of insulin is based on the experience made by the attending physician or patient. Typically, a physician prepares for a diabetic a dosing scheme that predetermines not only the quantity and frequency of insulin administrations to meet the basic insulin need but also contains instructions as to how to dose additional insulin administrations in response to elevated measuring values of the blood glucose concentration and meals. In this context, insulin administrations for meeting the basic insulin needs are called basal rate and additional insulin administrations related to meals are called bolus dose.

The general dosing instructions according to which a diabetic determines the dosing of the insulin administrations to be administered taking into consideration measuring values of the blood glucose concentration is called adjustment.

Suboptimal adjustment of the dosing of insulin administrations cannot be detected without further ado even on the basis of a series of measuring values of the blood glucose concentration, since the blood glucose concentration is subject to strong variations throughout the day even in healthy individuals. The article of N. Weintrob et al. titled "Glycemic patterns detected by continuous subcutaneous glucose sensing in children and adolescents with Type 1 Diabetes Mellitus treated by multiple injections vs continuous subcutaneous insulin infusion", Arch. Pediatr. Adolesc. 158, 677 (2004) follows the approach to assess continuously measured blood glucose concentrations with regard to the adjustment of dosing of insulin administration by means of time integrals of the blood glucose concentration.

In this procedure, an area above a base line that is predetermined by a threshold value of 180 mg/dl and below the blood glucose time curve is determined for a time period Δt of several days. This area is then divided by the time period Δt in order to obtain a parameter that characterizes a hyperglycemic disturbance of glucose metabolism. By the same procedure, a parameter characterizing hypoglycemic disturbances of glucose metabolism is determined by determining an area between a base line that is predetermined by a lower threshold value of 70 mg/dl and the blood glucose time curve for those times at which the blood glucose concentration is less than the respective threshold value.

The known method is called area-under-curve (AUC) calculation. A similar method for diagnosing diabetes is known from WO 2004/043230 A2. Herein, it is recommended to analyze, as a supplement, further features of a measured blood glucose concentration profile, for example the slope.

Methods of this type can be used to generally assess whether or not the insulin dosing of an insulin-dependent diabetic is adjusted well. However, it is essential for a specific recommendation concerning therapy or for optimization of adjustment to detect periods of glycemic instabilities in the glucose profile and their causal relationship to any insulin dosing or intake of food. In particular for persons with varying insulin sensitivity (so-called brittle diabetes), it is basically impossible to attain optimal adjustment of insulin dosing using known methods.

SUMMARY

It is therefore an object of the invention to devise a way in which a series of glucose concentration values of a body fluid of a diabetic can be better assessed for adjustment of the dosing of insulin administrations such that optimal insulin dosing can be attained for a diabetic at lesser effort. Particularly in patients with varying insulin sensitivity it is aimed to improve the adjustment of the dosing of insulin administrations by means of improved assessment of a series of glucose concentration measuring values.

This object is met by a method for the assessment of a series of glucose concentration values of a diabetic for adjustment of the dosing of insulin administrations, whereby glucose concentration values g(t1) to g(tn) that are related to time points t1 to tn that are distributed over a period of time of at least four hours, preferably at least six hours, are used as input parameters.

Moreover, the object is met by a device for assessment of a series of glucose concentration values of a body fluid of a diabetic for adjustment of the dosing of insulin administrations comprising a measuring unit for the measuring of glucose concentration measuring values g(t1) to g(tn) for time points t1 to tn that are distributed over a period of time of at least four hours, preferably at least six hours, a memory for storing the concentration values, and an analytical unit for analyzing the concentration values.

The body fluid of which glucose concentration values are considered according to the invention can, for example, be interstitial fluid or eye fluid measured by spectroscopy. Without limiting the general applicability, reference shall be made hereinafter to blood glucose concentration, since blood presumably is the body fluid most commonly referred to for investigating glucose metabolism. However, the invention provides for any other body fluid to be referred to for determining the glucose concentration.

The use of a weighting function allows blood glucose concentration values that deviate particularly strongly from the predetermined target range, for example 70 mg/dl to 180 mg/dl, to be considered at a greater weight when calculating the disturbance parameter as compared to concentration values that deviate only slightly from the target range. Therefore, according to the invention a disturbance parameter can be determined on the basis of function values of the weighting function, which disturbance parameter characterizes a disturbance of the tested glucose metabolism more correctly and thus facilitates improvement in the adjustment of the dosing of insulin administrations.

In this context, "disturbance" of the tested glucose metabolism is obviously not meant to be the disturbance caused by the disease itself that necessitates insulin administrations, but rather the non-compensated disturbance that remains despite the administration of insulin. The disturbance parameter determined according to the invention therefore characterizes possibly existing differences between the time course of the blood glucose concentration values of a diabetic treated by means of insulin administrations versus those of a healthy person.

It is important to note that the disturbance parameter determined according to the invention is not necessarily a one-dimensional parameter, i.e. an integer or a real number, but preferably is a set of values that characterize various aspects of the disturbance. For example, the disturbance parameter can be a pair of values of which a first value characterizes the severity of hyper- or hypoglycemic deviations from the target range and a second value characterizes the duration of these deviations. This pair of values could be supplemented, for example, by a third value that indicates the frequency of such disturbances.

The present method and device can be used for the assessment of concentration values that are measured over extended periods of time, at relatively short intervals a few minutes. Measuring techniques for measurements of this type have been described in the literature under the keyword continuous monitoring (CM). If a sufficiently long series of concentration values that were measured at sufficiently short time intervals is available, the method according to the invention can first be applied to individual time intervals that are included in the tested time interval and then the results determined for the individual time intervals can be used in a further step to determine the disturbance parameter by means of statistical methods.

Applying this procedure, disturbance values of the corresponding interval are initially used to calculate a characteristic disturbance number and, in a further step, the characteristic disturbance numbers of the individuals intervals are used to determine the disturbance parameter. In cases, in which only a relatively small number of concentration values is available such that only a single time interval is analyzed, the characteristic disturbance number and the disturbance parameters can be identical.

In the simplest case, the concentration values that are analyzed according to the invention each are measuring values. These can be processed in a suitable fashion, for example by applying statistical methods or suitable filter algorithms, in order to determine concentration values.

A large number of options are available for the exact form of the weighting function. For example penalty functions as are commonly used in the area of optimization problems can be used as weighting functions.

The weighting function preferably has a lesser slope in a target range of blood glucose concentration values than in a range adjacent to the target range. Preferably, this target range is between 50 mg/dl and 250 mg/dl, preferably between 70 mg/dl and 180 mg/dl. However, in a suitably selected weighting function, in particular a non-linear weighting function, the target range can just as well be selected to be significantly narrower, in an extreme case as a target value of, for example, 120 mg/dl.

The consecutive time points $t_1$ to $t_n$ of the glucose concentration values $g(t_1)$ to $g(t_n)$ are preferably separated by time intervals of less than 20 minutes, particularly preferred by time intervals of less than 10 min, in particular by time intervals of less than 5 min.

These and other features and advantages of the present invention will be more fully understood from the following detailed description of the invention taken together with the accompanying claims. It is noted that the scope of the claims is definitely by the recitations therein and not by the specific discussion of the features and advantages set forth in the present description.

BRIEF DESCRIPTION OF THE DRAWINGS

The following detailed description of the embodiments of the present invention can be best understood when read in conjunction with the following drawings, where like structure is indicated with like reference numerals and in which.

Skilled artisans appreciate that elements in the figures are illustrated for simplicity and clarity and have not necessarily been drawn to scale. For example, the dimensions of some of the elements in the figure may be exaggerated relative to other elements to help improve understanding of the embodiment(s) of the present invention.

In order that the invention may be more readily understood, reference is made to the following examples, which are intended to illustrate the invention, but not limit the scope thereof.

DETAILED DESCRIPTION

The following description of the preferred embodiment is merely exemplary in nature and is in no way intended to limit the invention or its application or uses.

Figure 1:
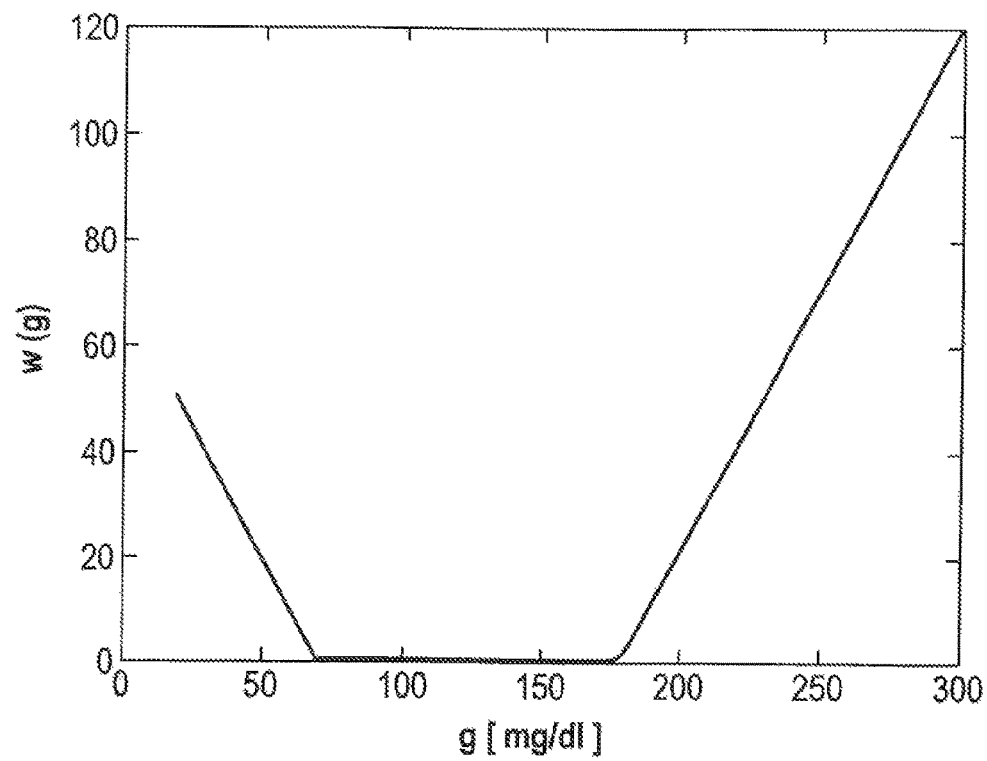
FIG. 1 shows an example of a weighting function.

FIG. 1 shows an example of a weighting/weight function w that is used to calculate disturbance values w(g) from blood glucose concentration values g. An essential feature of the weighting function is that it has a lesser slope in a target range of the blood glucose concentration than outside of the target range. A normoglycemic range of 70 mg/dl to 180 mg/dl was selected as target range in the example shown.

Outside of the target range, the weighting function shown increases linearly whereas it is constant within the target range. However, it is not obligatory to select as a weighting function such a function with linear sections. It is also feasible for the weighting function to increase non-linrearly outside of the target ranged. Moreover, it is not obligatory for the weighting function to be constant within the target range. For example a parabolic function with an apex at approx. 120 mg/dl can be selected as weighting function.

Figure 2:
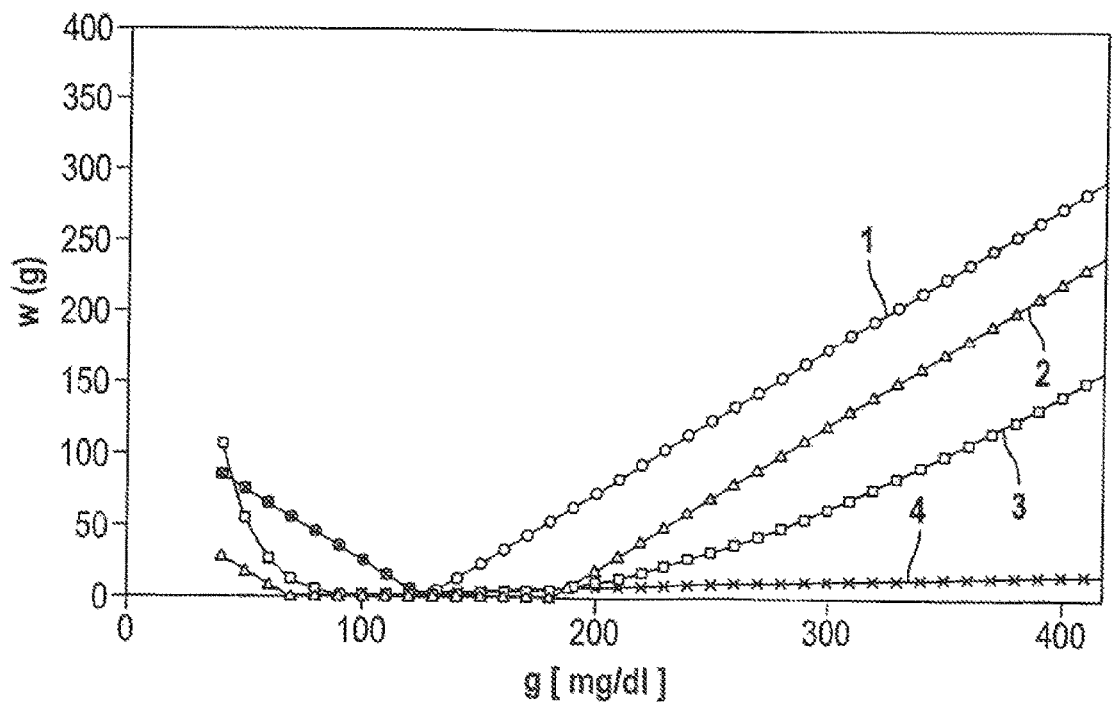
FIG. 2 shows further examples of a weighting function.

Further examples of suitable weighting functions are shown in FIG. 2. The weighting function 1 is an example of a weighting function, in which the target range was made much smaller such that it has collapsed into a point in the extreme case shown. Functions 2 and 3 are examples of asymmetrical weighting functions that weight hypoglycemic deviations from the target range more strongly than hyperglycemic deviations. In addition, weighting functions 2 and 3 are examples of non-linear weighting functions. Weighting function 3 is the Schlichtkrull index. Weighting function 4 corresponds to weighting function 1 over the hypoglycemic range. In the hyperglycemic range, the weighting function 4 initially increases in a section of it that is adjacent to the target range and then switches to being constant. As such, function 4 is an example to show that a weighting function does not have to have a greater slope than inside the target range in all places outside the target range. Rather, it is sufficient for the slope to be greater than in the target range just in a range adjacent to the target range.

Figure 3:
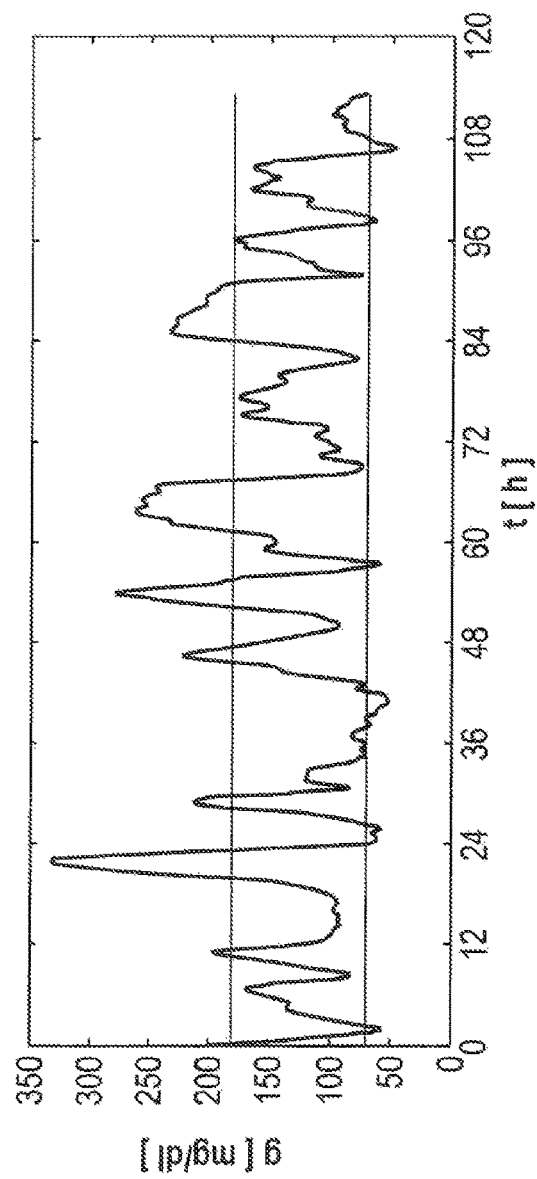
FIG. 3 shows an example of a series of blood glucose concentration values of a diabetic.

FIG. 3 shows an example of a series of blood glucose concentration values of a diabetic over a period of time of approx. 110 hours. The concentration values shown were determined at intervals of approx. 5 minutes. The target range of the weighting function shown in FIG. 1 is indicated by horizontal lines at blood glucose concentrations of 70 mg/dl and 180 mg/dl in FIG. 2. FIG. 3 shows that the blood glucose concentration is subject to major variations during the day. Both hyper- and hypoglycemic periods occur in a diabetic and are to be prevented by optimal adjustment of the dosing of insulin administrations.

For analysis, the concentration values of the series shown in FIG. 3 were initially used to calculate disturbance values as function values of the weighting function described by means of FIG. 1. These disturbance values were then analyzed for 12-hour time intervals each in that a mean value of the disturbance values of the corresponding time interval and the corresponding standard deviation were calculated. It is preferred to calculate the arithmetic mean as the mean value.

Figure 4:
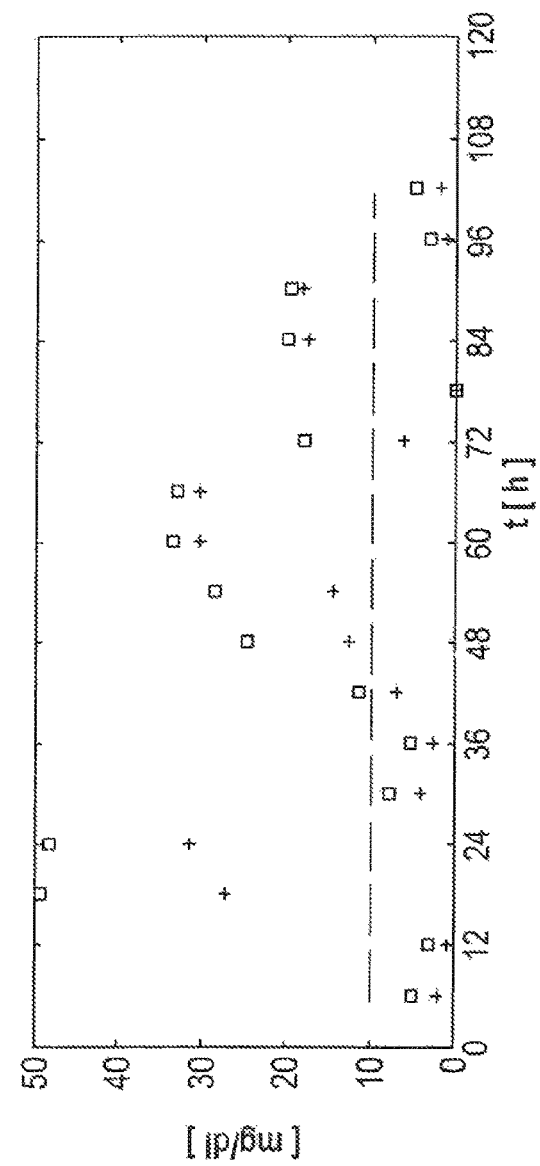
FIG. 4 shows means and standard deviations of the function values of the weighting function for overlapping time intervals of 12 hours each for the series shown in FIG. 3.

In FIG. 4 the mean value and the corresponding standard deviations of the disturbance values w(g) calculated for 12-hour time intervals are shown by crosses (+) and small boxes (□), respectively. Preferably, the time intervals are selected such as to be overlapping. In the exemplary embodiment shown, consecutive time intervals overlap by six hours each. The time intervals can be adjusted to the daily habits of a patient in the individual case such that they match, for example, the nocturnal sleep periods or waking periods of the patient. It is also favorable to select the time intervals according to pre- and postprandial phases such that therapeutically relevant correlations can be demonstrated more easily.

As a pair of values, the mean values and corresponding standard deviations shown in FIG. 4 represent a characteristic disturbance number for the respective time interval that characterizes the type and/or severity of a disturbance of the tested glucose metabolism. In this context, it is obviously not obligatory to use the mean values and standard deviations themselves as components of the characteristic disturbance numbers. Any measure of the mean value and standard deviations can be used as component of characteristic disturbance numbers just as well. In the simplest case the measure is a multiple of the mean value and/or standard deviation or it is calculated from the mean and/or standard deviation by adding a constant term.

The characteristic disturbance numbers of the individual time intervals are then used in a statistical analysis to determine a disturbance parameter that is then assigned to one of at least two predetermined classes. Recommendations concerning the adjustment of the dosing of insulin administrations are dedicated to these classes such that the adjustment of the dosing of the insulin administrations can be improved by this means.

Figure 5:
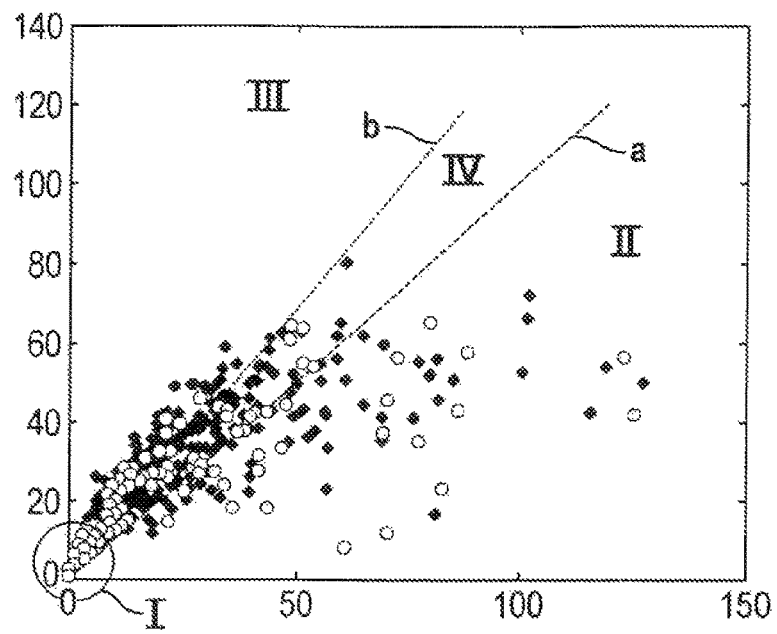
FIG. 5 shows standard deviations and means of function values of the weighting function for various subjects.

FIG. 5 shows entries of standard deviations and mean values of function values of the weighting function that were determined a described above. The ordinate shows the standard deviations and the abscissa show the mean values of the function values of the weighting function for time intervals of 12 hours each. FIG. 5 shows results of the analysis of series of blood glucose concentration values that were measured in 45 subjects. In this context, each series was measured over a time period of approx. 5 days. Results for type 1 diabetics and insulin-dependent type 2 diabetics are indicated by diamonds and circles, respectively.

FIG. 5 shows that there is no significant difference between the results for type 1 diabetics and the results for type 2 diabetics. This is not surprising since the adjustment of the dosing of insulin administrations is associated with essentially the same difficulties in both cases. As has been explained by means of FIG. 4, a mean value and the corresponding standard deviation of the function values of the weighting function are a pair of values that represents a characteristic disturbance number for the respective time interval of a tested series of concentration values. These characteristic disturbance numbers can be classified in four different classes.

Characteristic disturbance numbers that are drawn within a circle around the origin of the coordinate system in FIG. 5 belong to first class I. Characteristic disturbance numbers of class I are so small that the adjustment of the dosing of insulin administrations can be presumed to be optimal. In these cases, no change of the adjustment is required.

Characteristic disturbance numbers that are shown in FIG. 5 to be below a straight line a through the origin that is indicated by dashes are assigned to a second class II. Class II includes cases, in which the mean values of the disturbance values are larger than the corresponding standard deviations. For this reason, characteristic disturbance numbers of class II are indicative of cases, in which a major deviation of the blood glucose concentration values from the target range occurred for extended periods of time. Characteristic disturbance numbers of class II thus lead to the conclusion that the basal rate of insulin administrations is poorly titrated. If the observed deviation of the blood glucose concentration from the target range is a hypoglycemic deviation, the basal rate must be reduced, whereas the basal rate must be increased if hyperglycemic deviations are evident.

Characteristic disturbance numbers that are shown in FIG. 5 to be above a straight line b through the origin that is indicated by dots are assigned to a third class III. Characteristic disturbance numbers of class III reflect that the standard deviation of the function values of the weighting function, i.e. the disturbance values, of the mean values of a tested time interval are significantly larger than the mean value itself, for example 20% larger. Consequently, class III includes cases, in which the disturbance values are subject to strong short-term fluctuations. This in turn means that the underlying series of concentration values is characterized by short-term deviations from the target range. Usually, such deviations occur in connection with meals or upon physical exercise such that for optimizing the adjustment of the bolus doses, i.e. the additional insulin administrations in connection with meals or physical exercise should be adjusted.

Characteristic disturbance numbers that are shown in FIG. 5 between the dotted straight line b through the origin and the dashed straight line a through the origin are assigned to a fourth class IV. In cases of this type, the mean values and the standard deviations of the function values of the weighting function are approximately equal in size in the tested time interval such that both the basal rate and the bolus of insulin administrations need to be checked and adjusted.

In the example illustrated by means of FIG. 5, the index of the respective class (i.e. the number I, II, III or IV) is the disturbance parameter that was determined by means of a statistical analysis of the disturbance values. To each of these disturbance parameters, i.e. to each of these classes, is assigned a qualitative recommendation specifying how the adjustment of the dosing of insulin administrations is to be calibrated. If, in addition to a series of concentration values, further relevant data in terms of the time course of the blood glucose concentration, in particular with regard to insulin administrations given and bread units taken in, are recorded and analyzed, this data and the recommendations assigned to the classes can be used also to calculate the required insulin doses and the points in time, at which these are to be administered. For this purpose, quantitative data concerning the deviations of the blood glucose concentration values from the target range must be taken into consideration. Alternatively, the characteristic disturbance numbers for the respective class can first be analyzed qualitatively, whereby the degree of deviation is recorded and taken into consideration in the calculation of the insulin doses thereafter.

In the procedure described above, the disturbance parameter was calculated on the basis of the mean values of the disturbance values and standard deviation of the disturbance values. Supplementary or alternatively, the disturbance parameter or some of its components can be determined, for example, by assigning the disturbance values to one of multiple metabolic states each and then determining how long the various states persist and/or how frequently changes of states occur. In this context, one component of the disturbance parameter can, for example, be a measure for the period of time for which the corresponding state persists. Another component of the disturbances parameter can be a measure for the frequency of the change of states.

Disturbance values can be assigned to states of glucose metabolism, for example, by means of predetermined threshold values. Rather than using a disturbance function, as is shown in FIGS. 1 and 2, a procedure of this type can use a step function that, for example, takes the value 0 in a target range (normoglycemic range), takes the value −1 below the target range (hypoglycemic range), and takes the value +1 above the target range (hyperglycemic range).

If the number of changes of states within a tested time interval exceeds a predetermined threshold value, this indicates an instability in the adjustment of the insulin administrations and thus should be taken into consideration in the disturbance parameter. The disturbance parameter can, for example, include, in addition, a value that indicates the number of changes of states or is calculated from this number.

The method as described can be utilized by a hand-held analytical device that is used by diabetics to self-monitor their blood sugar level. By this means, useful hints can be provided to a diabetic by means of the hand-held device concerning how the required insulin administrations can be adjusted better to the existing needs. In particular, the use of a hand-held device utilizing the described method all a diabetic to effect minor calibrations of the adjustment himself and—if a need for major adjustment exists—to be referred to a physician.

Figure 6:
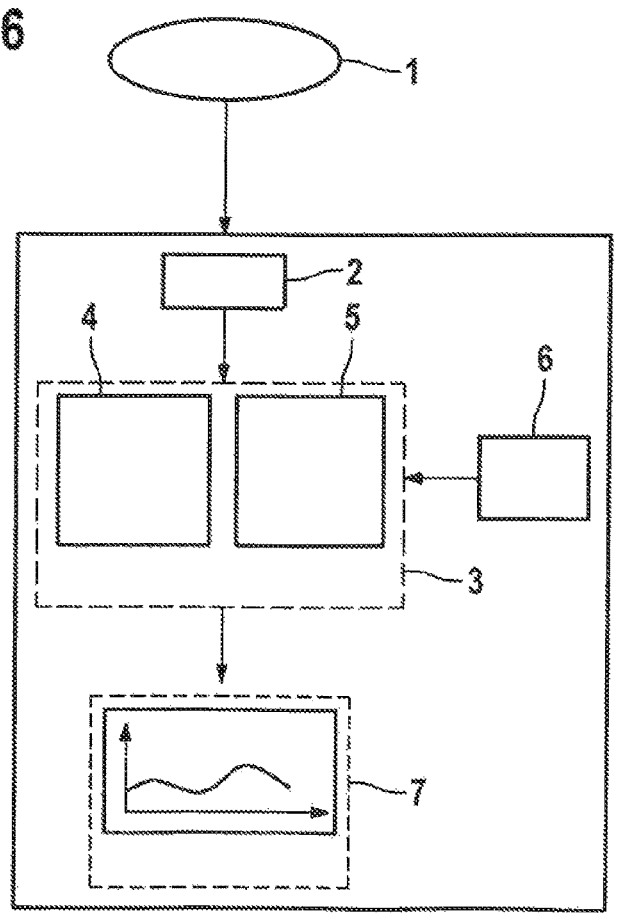
FIG. 6 shows a schematic representation of a device for carrying out a method according to the invention.

FIG. 6 shows the essential components of a device of this type. A measuring unit 1 uses a sensor to measure $t_n$ measuring values at consecutive time points. This measuring signal is then transmitted to a receiver 2—in a wireless fashion in the case shown—from which the measuring signal is transferred to an analytical unit 3 that contains a microprocessor 4 and a data memory 5. Data, for example data concerning insulin administrations given or bread units taken up, and commands can also be transmitted to the analytical unit via an input unit 6. The output of results is effected by means of an output unit 7 that can comprise a display and other common output means. It is self-evident that the data processing in the analytical unit 3 is effected by digital means and that corresponding transducers for converting analog signals into digital signals are provided. Particularly well-suited are implantable sensors that can be used to determine blood glucose concentration values in relative short time intervals, for example 5 min.

The method described can also be used for a device that comprises, in addition to the measuring unit 2, memory 5, and analytical unit 3, an insulin pump that is controlled by the analytical unit 3 by taking into consideration the recommendation of the class thus determined to which the disturbance parameter was assigned to belong.

Other devices for insulin administration can be used instead of an insulin pump, for example so-called insulin pens, which are ball-point pen-sized injection devices. It is preferable for information concerning the administered insulin dose to be transmitted by wireless means from the device used for insulin administration, for example the insulin pump or an insulin pen, to the analytical unit 3. This can be effected for example after each administration of insulin or after predetermined time intervals. Supplementing this, further peripheral devices can be used, for example devices in which information concerning the bread units of various foods is stored such that, upon request, corresponding estimates for an ingested meat can be transmitted to the analytical unit 3 of the device described. It is self-evident that such information can also be stored in a memory of the analytical unit 3.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

For the purposes of describing and defining the present invention it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the invention in detail and by reference to specific embodiments thereof, it will be apparent that modification and variations are possible without departing from the scope of the invention defined in the appended claims. More specifically, although some aspects of the present invention are identified herein as preferred or particularly advantageous, it is contemplated that the present invention is not necessarily limited to these preferred aspects of the invention.

What is claimed is:

1. A method for determining a disturbance parameter characterizing a disturbance of a tested glucose metabolism that is manifest despite the administration of insulin to adjust dosing of insulin administration, the method comprising:
relating glucose concentration values $g(t_1)$ to $g(t_n)$ to time points $t_1$ to $t_n$ that are distributed over a period of time of at least four hours;
using the glucose concentration values $g(t_1)$ to $g(t_n)$ as input parameters to a processor to calculate disturbance values $w(g(t1))$ to $w(g(tn))$ as function values of a weight function w, wherein the weight function w has a lesser slope in a target range of the glucose concentration values $g(t_1)$ to $g(t_n)$ than in a range that is adjacent to the target range;
determining the disturbance parameter on a processor from the disturbance values, wherein the disturbance parameter characterizes a type and/or severity of a disturbance of the tested glucose metabolism that is manifest despite the administration of insulin;
assigning the disturbance parameter on a processor by use of predetermined parameter ranges to one of at least two predetermined classes, wherein with each of the classes corresponding to recommendations for adjustment of the dosing of the insulin administrations are generated as output parameters;
signaling an output unit to output a recommendation for adjustment of the dosing of the insulin administrations corresponding to the assigned class; and
controlling an insulin administration device to adjust the dosing of the insulin administration in response to the recommendation.

2. The method according to claim 1, wherein the disturbance parameter is a multi-dimensional parameter with multiple components.

3. The method according to claim 1, wherein determining the disturbance parameter further comprises a step, in which a mean value of the disturbance values is calculated.

4. The method according to claim 3, wherein determining the disturbance parameter comprises a step, in which a standard deviation of the disturbance values from said mean value is calculated.

5. The method according to claim 4, wherein one component of the disturbance parameter is a measure of the standard deviation of the disturbance values from the mean value.

6. The method according to claim 3 wherein one component of the disturbance parameter is a measure of the mean value of the disturbance values.

7. The method according to claim 1, wherein the calculation of the disturbance parameter comprises a step, in which the disturbance values are assigned to one each of multiple states and it is determined how long the various states persist and/or how frequently changes of states occur.

8. The method according to claim 7, wherein one component of the disturbance parameter is a measure of the period of time for which one of these states persists.

9. The method according to claim 7, wherein one component of the disturbance parameter is a measure of the frequency of the changes of states.

10. A method for determining a disturbance parameter characterizing a disturbance of a tested glucose metabolism that is manifest despite the administration of insulin to adjust dosing of insulin administration, the method comprising:
relating glucose concentration values $g(t_1)$ to $g(t_n)$ to time points $t_1$ to $t_n$ that are distributed over a period of time of at least four hours;
using the glucose concentration values $g(t_1)$ to $g(t_n)$ as input parameters to a processor to calculate disturbance values $w(g(t1))$ to $w(g(tn))$ as function values of a weight function w, the weight function w being configured to give more weight to a large deviation between the glucose concentration values $g(t_1)$ to $g(t_n)$ and a target range of glucose concentration values than a small deviation between the glucose concentration values $g(t_1)$ to $g(t_n)$ and the target range; wherein for multiple time intervals that are each included in the period of time, the disturbance values of the respective time intervals are used to calculate a respective characteristic disturbance numbers;
using the characteristic disturbance numbers to determine the disturbance parameter on a processor, wherein the disturbance parameter characterizes a type and/or severity of a disturbance of the tested glucose metabolism that is manifest despite the administration of insulin;
signaling an output unit to output a recommendation for adjustment of a dosing of the insulin administrations corresponding to the type and/or severity of the disturbance; and
controlling an insulin administration device to adjust the dosing of the insulin administration in response to the recommendation.

11. The method according to claim 10, further comprising assigning the disturbance parameter on a processor by use of predetermined parameter ranges to one of at least two predetermined classes, wherein with each of the classes correspond to recommendations for adjustment of the dosing of the insulin administrations and are generated as output parameters.

12. The method according to claim 10, wherein the time intervals, for which the characteristic disturbance numbers each are calculated, overlap.

13. The method according to claim 1, wherein the weight function used to calculate the disturbance values is a function with linear section(s).

14. The method according to claim 13, wherein the weight function is constant in the target range.

15. A system for assessment of a series of glucose concentration values of a body fluid of a diabetic for adjustment of the dosing of insulin administrations, the system comprising:
a measuring unit comprising a sensor configured to measure glucose concentration values $g(t_1)$ to $g(t_n)$ for time points $t_1$ to $t_n$ that are distributed over a period of time of at least four hours;
a memory for storing the concentration values;
an analytical unit for analyzing the concentration values;
a receiver in communication with the measuring unit and the analytical unit; the receiver being configured to transfer the measured glucose concentration values from the measuring unit to the analytical unit;
wherein the analytical unit is adapted to use the glucose concentration values $g(t_1)$ to $g(t_n)$ as input parameters to calculate disturbance values $w(g(t1))$ to $w(g(tn))$ as function values of a weight function w, determine a disturbance parameter from the disturbance values, and assign the disturbance parameter to one of at least two predetermined classes, each of said classes corresponding to recommendations concerning the optimal dosing of insulin administrations being dedicated such that these recommendations can be provided for adjustment of the dosing of the insulin administrations;

wherein the weight function w has a lesser slope in a target range of the glucose concentration values $g(t_1)$ to $g(t_n)$ than in a range that is adjacent to the target range; and an insulin administration device coupled to the analytical unit, the insulin administration device being controlled by the analytical unit to adjust the dosing of the insulin administration in response to the recommendation corresponding to the assigned predetermined class.

16. The system according to claim 15 wherein the system comprises an input unit by means of which relevant data in terms of the time course of the glucose concentration, can be entered or received by another device, and in that the analytical unit uses this data and the recommendations assigned to the classes to calculate required insulin doses.

17. The system according to claim 16, wherein the system comprises an output unit for output of a recommendation regarding the dosing of the insulin administration of the diabetic.

18. The system according to claim 15, wherein the insulin administration device is an insulin pump that is controlled by the analytical unit taking into consideration the recommendation of the class to which the disturbance parameter was assigned.

19. The method according to claim 1, wherein a recommendation for one of the at least two predetermined classes is to adjust a basal rate, a recommendation of another of the at least two predetermined classes is to adjust bolus doses, and a recommendation of yet another of the at least two predetermined classes is to adjust both a basal rate and a bolus doses.

* * * * *